United States Patent
Matsuoka et al.

(10) Patent No.: US 8,285,004 B2
(45) Date of Patent: Oct. 9, 2012

(54) LINE OF SIGHT DETECTING DEVICE AND METHOD

(75) Inventors: Miki Matsuoka, Osaka (JP); Atsushi Irie, Nara (JP)

(73) Assignee: OMRON Corporation, Kyoto (JP)

( * ) Notice: Subject to any disclaimer, the term of this patent is extended or adjusted under 35 U.S.C. 154(b) by 839 days.

(21) Appl. No.: 12/428,795

(22) Filed: Apr. 23, 2009

(65) Prior Publication Data

US 2009/0268944 A1  Oct. 29, 2009

(30) Foreign Application Priority Data

Apr. 28, 2008  (JP) .................................. 2008-117106

(51) Int. Cl.
*G06K 9/00*  (2006.01)

(52) U.S. Cl. ....................... 382/117; 382/118

(58) Field of Classification Search .................. None
See application file for complete search history.

(56) References Cited

U.S. PATENT DOCUMENTS 5,912,721 A * 6/1999 Yamaguchi et al. .......... 351/210
7,657,062 B2 * 2/2010 Pilu ................................ 382/103

FOREIGN PATENT DOCUMENTS

| JP | 2000-083228 A | 3/2000 |
|----|---------------|--------|
| JP | 2003-271932 A | 9/2003 |
| JP | 2005-340974 A | 12/2005 |
| JP | 2006-119408 A | 5/2006 |
| JP | 2006-141862 A | 6/2006 |
| JP | 2007-265367 A | 10/2007 |

OTHER PUBLICATIONS

Examination Report Issued in JP Application No. 2008-117106, Dated Feb. 2, 2012 (6 Pages With English Translation).
Patent Abstracts of Japan, Publication No. 2003-271932, dated Sep. 26, 2003, 1 page.
Patent Abstracts of Japan, Publication No. 2005-340974, dated Dec. 8, 2005, 1 page.
Patent Abstracts of Japan, Publication No. 2006-119408, dated May 11, 2006, 1 page.
Patent Abstracts of Japan, Publication No. 2000-083228, dated Mar. 21, 2000, 1 page.
Patent Abstracts of Japan, Publication No. 2007-265367, dated Oct. 11, 2007, 1 page.

* cited by examiner

*Primary Examiner* — Brian P Werner
(74) *Attorney, Agent, or Firm* — Osha Liang LLP (57) ABSTRACT

A line of sight detecting method includes estimating a face direction of an object person based on a shot face image of the object person, detecting a part of an eye outline in the face image of the object person, detecting a pupil in the face image of the object person, and estimating the direction of a line of sight of the object person based on the correlation of the pupil position in the eye outline and the face direction with respect to the direction of the line of sight, and the pupil position and the face direction of the object person.

4 Claims, 11 Drawing Sheets

LINE OF SIGHT DETECTING DEVICE AND METHOD

BACKGROUND OF THE INVENTION

1. Field of the Invention

The present invention relates to a line of sight detecting device and method, and more particularly, relates to a line of sight detecting device and method capable of detecting more accurate direction of the line of sight.

2. Description of Related Art

Conventionally, it is proposed to decide a direction of a line of sight (hereinafter referred to as a LOS) based on the center position of a pupil in a reference image when a user is looking at five positions, i.e., the center position and the four corners of a display and the center position of a pupil in a detected image for detecting the LOS. (see Japanese patent publication No. 2006-141862)

However, the center position of a pupil in the detected image is varied depending on a direction and a position of a user's face even if the user's looking directions are same. Therefore it is difficult to decide an accurate direction of LOS only by using the center position of a pupil. The Japanese patent publication suggests that the direction and position of the user's face are detected and combined with the direction of pupil to decide the direction of the user's LOS. However, the specific processes are not described.

The present invention has been created to make it possible to detect an accurate direction of a LOS.

SUMMARY

A LOS detecting device according to an aspect of the present invention includes a face-direction estimation means for estimating a face-direction of an object person based on a shot face image of the object person to detect the LOS direction, eye detection means for detecting a part of an eye-outline of in the face image of the object person, pupil detection means for detecting a pupil in the face image of the object person and LOS direction estimation means for estimating the LOS direction of the object person based on the correlation of the pupil position in the eye-outline and the face direction with respect to the LOS direction, and the pupil position and the face direction of the object person The LOS detecting device according to an aspect of the present invention estimates the face direction of the object person based on the shot face image of the object person to detect the LOS direction, detects a part of the eye-outline in the face image of the object person, detects the pupil in the face image of the object person and estimates the LOS direction of the object person based on the correlation of the pupil position in the eye-outline and the face direction with respect to the LOS direction, and the pupil position and the face direction of the object person. Thus, an accurate LOS direction can be detected.

The face direction estimation means, eye detection means, pupil detection means and LOS direction estimation means are configured with a CPU (Central Processing Unit).

The LOS direction estimation means can estimate the LOS direction of the object person based on the correlation of the position of the pupil, the face direction and the shape of the eye-outline with respect to the LOS direction, and the pupil position, face direction and the shape of the eye-outline of the object person. Thus, an accurate LOS direction can be detected.

The LOS direction detection device further includes correlation analysis means for analyzing the correlation based on the pupil position data in multiple combinations of the face directions and the LOS directions, wherein the LOS direction estimation means can estimate the LOS direction of the object person based on the correlation analyzed by the correlation analysis means. Thus, an accurate LOS direction can be detected flexibly responding to a use condition and a use environment.

The correlation analysis means is configured with a CPU (Central Processing Unit).

The LOS detecting method according to an aspect of the present invention includes steps of estimating the face direction of the object person based on a shot face image of the object person to detect the LOS direction, detecting a part of the eye-outline in the face image of the object person, detecting the pupil in the face image of the object person and estimating the LOS direction of the object person based on the correlation of the pupil position in the eye-outline and the face direction with respect to the LOS direction, and the pupil position and the face direction of the object person The LOS detecting method according to an aspect of the present invention estimates the face direction of an object person based on a shot face image of the object person to detect the LOS direction, detects a part of the eye-outline in the face image of the object person, detects the pupil in the face image of the object person and estimates the LOS direction of the object person based on the correlation of the pupil position in the eye-outline and the face direction with respect to the LOS direction, and the pupil position and the face direction of the object person Thus, an accurate LOS direction can be detected.

The steps of estimating the face direction, detecting the eye-outline, detecting the pupil and estimating the LOS direction are executed by a CPU (Central Processing Unit).

DETAILED DESCRIPTION

In the following detailed description, reference is made to the accompanying FIGS. 1 through 11, which illustrate the described embodiments. The embodiments are described in sufficient detail to enable those skilled in the art to make and use them.

Figure 1:
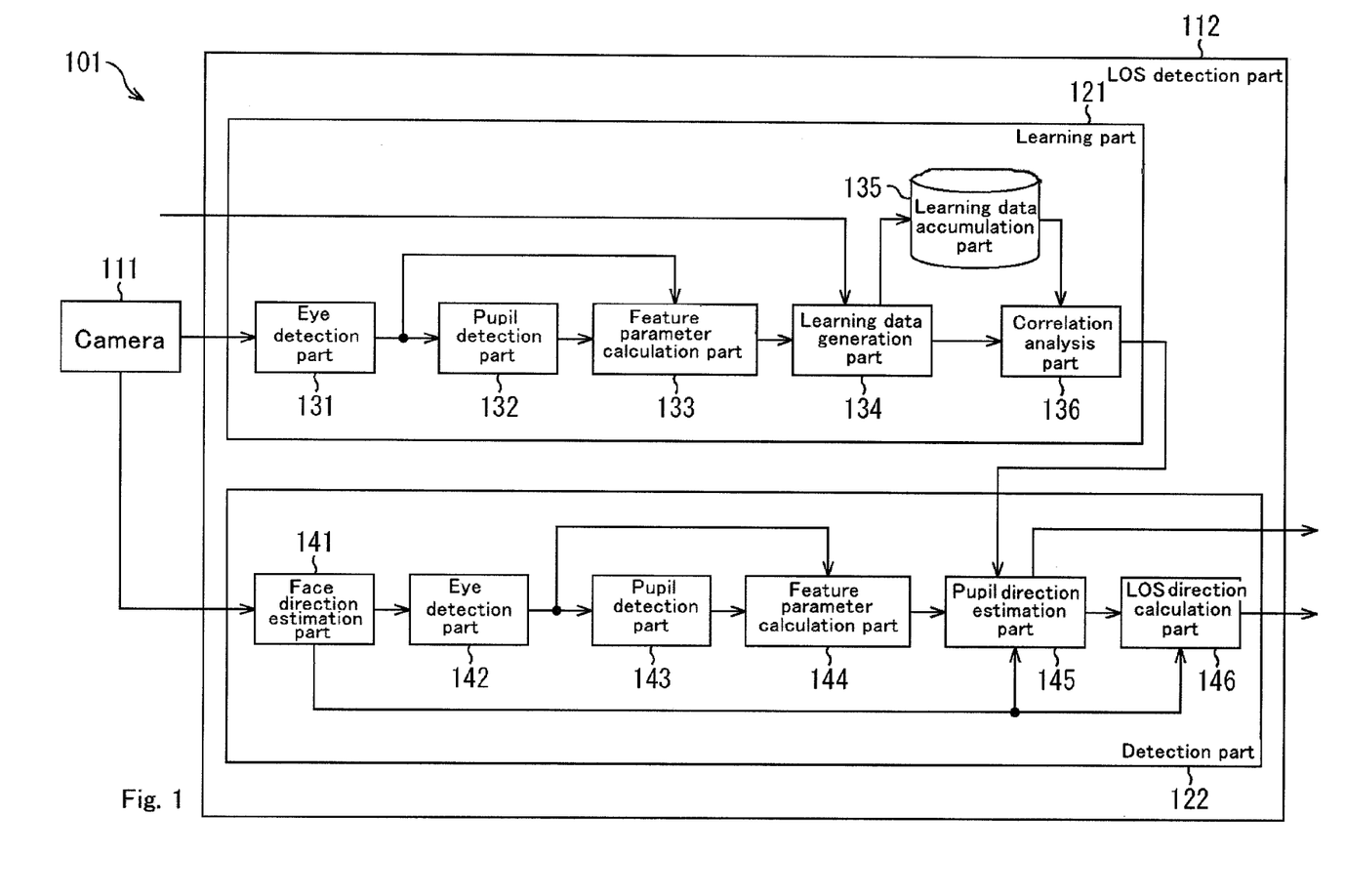
FIG. 1 is a block diagram showing an embodiment of a LOS detection system according to the present invention.

FIG. 1 is a block diagram showing an embodiment of a LOS detection system according to the present invention. The LOS detection system shown in FIG. 1 is configured to include a camera 111 and a LOS detection device 112.

The camera 111 takes a shot of the face of a person whose LOS is detected (hereinafter referred to as an object person) and send the shot image (hereinafter referred to as a face image) to the LOS detection device 112.

The LOS detection device 112 detects the pupil direction and LOS direction of the object person appearing in the face image and outputs the data including the detection results to the latter part of the LOS detection device 112.

Figure 2:
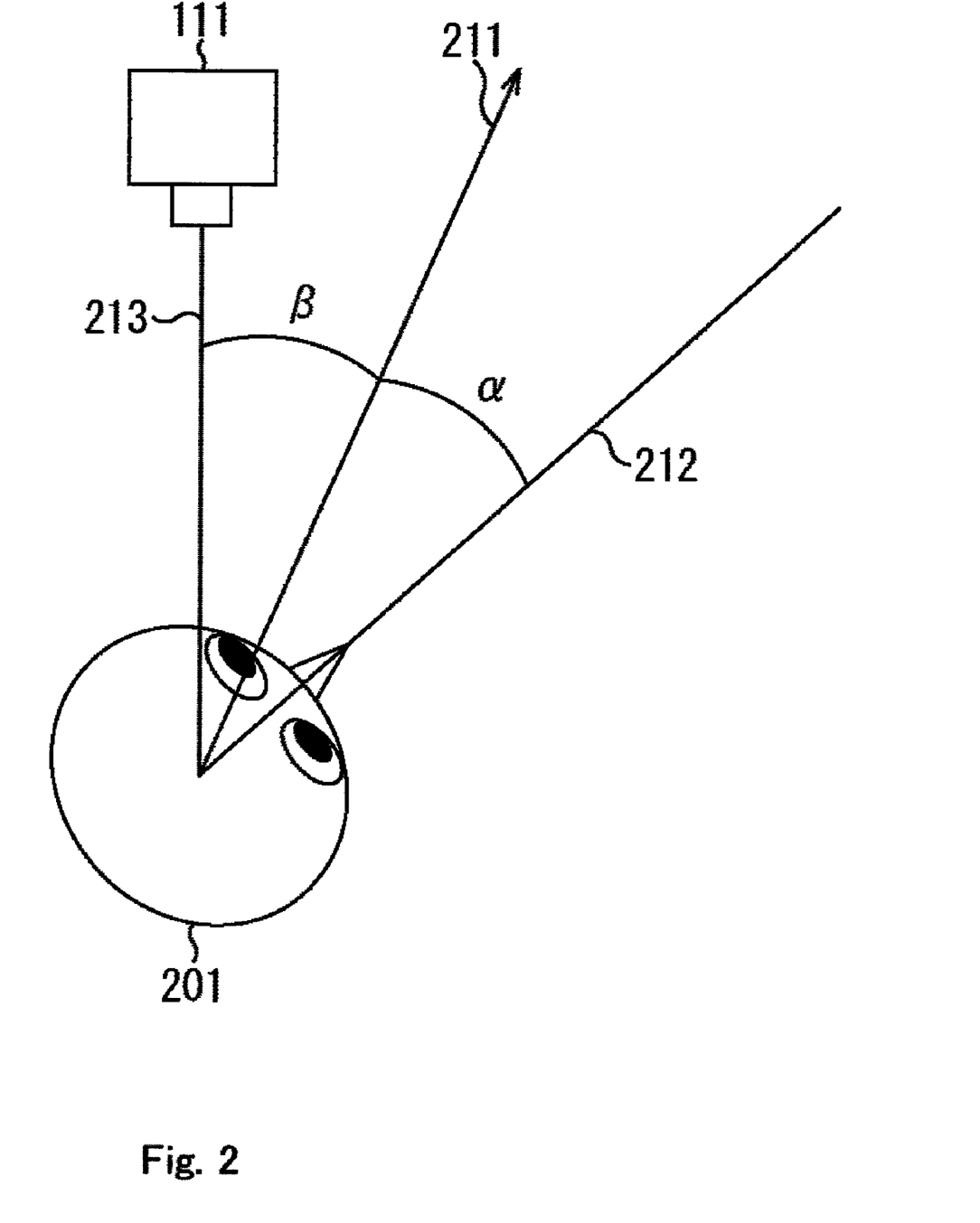
FIG. 2 is a schematic view illustrating a face direction, a pupil direction and a LOS direction.

Next, the face direction, the pupil direction and the LOS direction are defined in reference to FIG. 2. The arrow 211 shows the direction of the pupil of the object person 201, the axis 212 shows the direction of the face of the object person 201 (the front face direction of the face of the object person 201) and the optical axis 213 shows the optical axis of the camera 111.

First, the face direction of the object person 201 is defined in reference to the optical axis 213 of the camera 111, in other words, as the face direction viewed from the camera 111. For example, FIG. 2 shows that the face direction of the object person 201 is in the direction of an axis 212 in reference to the optical axis 213, i.e. in the direction at an angle of α+β on the right. The face direction on the right side or the upper side in reference to the optical axis 213 is a positive direction, while the face direction on the left side or the lower side in reference to the optical axis 213 is a negative direction.

Secondly, the pupil direction of the object person 201 is defined in reference to the face direction of the object person 201, in other words, as the LOS direction in reference to the face direction of the object person 201. For example, FIG. 2 shows that the pupil direction of the object person 201 is in the direction of an arrow 211 in reference to the axis 212, i.e. in the direction at an angle of α on the left. The pupil direction on the right side or the upper side in reference to the axis 212 is a positive direction, while the pupil direction on the left side or the lower side in reference to the axis 212 is a negative direction.

Further, the LOS direction of the object person 201 is defined as the direction of the pupil in reference to the optical axis 213 of the camera 111, in other words, as the LOS direction of the object person 201 viewed from the camera 111. For example, FIG. 2 shows that the LOS direction of the object person 201 is in the direction of an arrow 211 in reference to the optical axis 213, i.e. in the direction at an angle of β on the right. The LOS direction on the right side or the upper side in reference to the optical axis 213 is a positive direction, while the LOS direction on the left side or the lower side in reference to the optical axis 213 is a negative direction.

1

Going back to FIG. 1, the LOS detection device 112 is configured to include a learning part 121 and a detection part 122. The learning part 121, as described later in reference to FIG. 3, etc., learns the correlation of the pupil position in the eye-outline and the face direction with respect to the pupil direction or learns the correlation of the pupil position in the eye-outline, the face direction and the shape of the eye-outline with respect to the LOS direction, based on the face image and the face data including the face direction and pupil direction of the object person when the face image is shot. The learning part 121 is configured with an eye detection part 131, a pupil detection part 132, a feature parameter calculation part 133, a leaning data generation part 134, a learning data accumulation part 135 and a correlation analysis part 136.

The eye detection part 131, as described later in reference to FIG. 3, etc., detects a part of the outline of the eye in the face image of the object person using a given method. The eye detection part 131 sends the face image and the data showing the detection results to the pupil detection part 132. Further, the eye detection part 131 sends the data showing the detection results to the feature parameter calculation part 133.

The pupil detection part 132, as described later in reference to FIG. 3, etc., detects the pupil in the face image of the object person using a given method. The pupil detection part 132 sends the data showing the detection results to the feature parameter calculation part 133.

The feature parameter calculation part 133, as described later in reference to FIG. 3, etc., calculates a feature parameter showing the pupil position in the eye-outline or calculates a feature parameter showing the pupil position in the eye-outline and the shape of the eye-outline, based on the eye-outline and the detection results of the pupil of the object person. The feature parameter calculation part 133 sends the data showing the calculated feature parameter to the learning data generation part 134.

The learning data generation part 134 generates learning data correlating the pupil direction of the object person with the feature parameter calculated based on the face direction when the face image is shot and the face image. The learning data generation part 134 accumulates the generated learning data in the learning data accumulation part 135. The learning data generation part 134 notifies to the correlation analysis part 136 that a certain amount of the learning data has been accumulated in the learning data accumulation part 135.

The correlation analysis part 136 analyzes the correlation of the face direction and the feature parameter with respect to the pupil direction based on the learning data accumulated in the learning data accumulation part 135 and sends the data showing the analysis results to the pupil direction estimation part 145 in the detection part 122.

The detection part 122, as described later in reference to FIG. 7, etc., detects the pupil direction and the LOS direction of the object person based on the face image of the object person shot by the camera 111 and the correlation learned by the learning part 121. The detection part 122 is configured to include a face direction estimation part 141, an eye detection part 142, a pupil detection part 143, a feature parameter calculation part 144, a pupil direction estimation part 145 and a LOS direction calculation part 146.

The face direction estimation part 141 estimates the face direction of the object person based on the face image of the object person shot by the camera 111 using a given method. The face direction estimation part 141 sends the face image and the data showing the estimation results to the eye detection part 142. The face direction estimation part 141 sends the data showing the estimation results to the pupil direction estimation part 145 and the LOS direction calculation part 146.

The eye detection part 142, in the same process as that of the eye detection part 131, detects a part of the eye-outline in the face image of the object person using a given method. The eye detection part 142 sends the face image and the data showing the detection results to the pupil detection part 132. Further, the eye detection part 142 sends the data showing the detection results to the feature parameter calculation part 144.

The pupil detection part 143, in the same process as that of the pupil detection part 132 in the learning part 121, detects the pupil in the face image of the object person using a given method. The pupil detection part 143 sends the data showing the detection results to the feature parameter calculation part 144.

The feature parameter calculation part 144, in the same process as that of the feature parameter calculation part 133 in the learning part 121, calculates the feature parameter based on the eye-outline of the object person and the detection results of the pupil. The feature parameter calculation part 144 sends the data showing the calculated feature parameter to the pupil direction estimation part 145.

The pupil direction estimation part 145 estimates the pupil direction of the object person based on the correlation of the face direction and the feature parameter with respect to the pupil direction, the face direction and the feature parameter of the object person. The pupil direction estimation part 145 sends the data showing the estimated pupil direction to the LOS direction calculation part 146 and the latter part of the LOS detection device 112.

The LOS direction calculation part 146 calculates the LOS direction of the object person based on the face direction and the pupil direction of the object person. The LOS direction calculation part 146 sends the data showing the calculated LOS direction to the latter part of the LOS detection device 112.

Next, the operation of the LOS detection system 101 is described in reference to FIG. 3 through FIG. 7. First, the learning process executed by the LOS detection device 112 is described in reference to the flowchart shown in FIG. 3.

In step S1, the learning part 121 obtains the face data. Using the camera 111, the user takes a shot of the face of the object person with a face direction and a pupil direction. The user inputs to the learning part 121 the face image and the data showing the face direction and the pupil direction when the face image is shot. The eye detection part 131 in the learning part 121 obtains the face image from the inputted face data, and the learning data generation part 134 obtains the data showing the face direction and the pupil direction of the object person from the inputted face data.

In step S2, the eye detection part 131 detects the eye-outline in the face image of the object person using a given method. The eye detection part 131 sends the face image and the data showing the detection results to the pupil detection part 132. Further, the eye detection part 131 sends the data showing the detection results to the feature parameter calculation part 133.

In step S3, the pupil detection part 132 detects the pupil in the face image of the object person using a given method. The pupil detection part 132 uses the detection results of the eye-outline of the object person as necessary. The pupil detection part 132 sends the data showing the detection results to the feature parameter calculation part 133.

In step S4, the feature parameter calculation part 133 calculates the feature parameter based on the eye-outline and the pupil detection results of the object person. The feature parameter calculation part 133 sends the data showing the calculated feature parameter to the learning data generation part 134.

Figure 4:
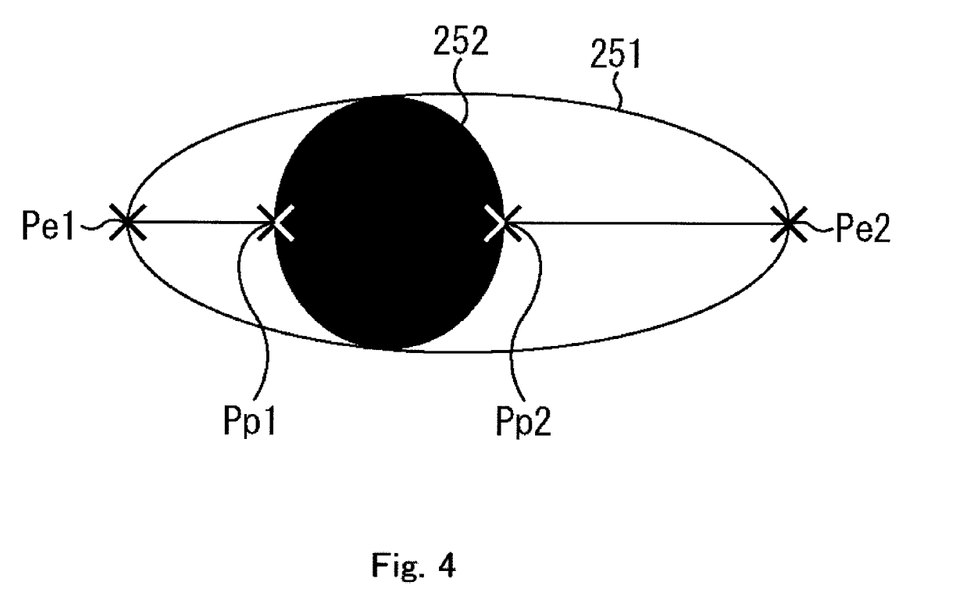
FIG. 4 is a schematic view illustrating a feature parameter.
Figure 5:
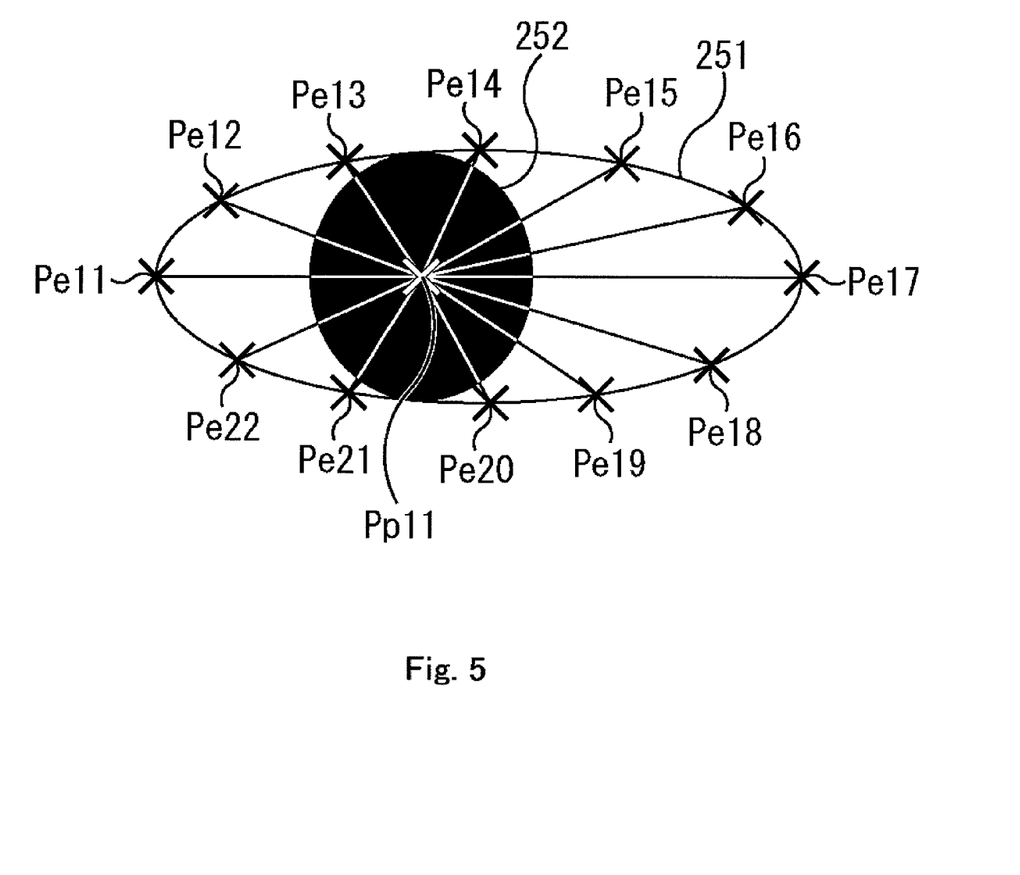
FIG. 5 is a schematic view illustrating another feature parameter.

In reference to FIGS. 4 and 5, the specific processes of the steps S2 through S4 are described. Using a given method, the eye detection part 131 detects the left and the right ends (Pe1 and Pe2) of an eye which are parts of the outline of the eye 251 as shown in FIG. 4. The method of detecting the both ends of the eye is not limited to a particular method. The methods capable of detecting them more accurately, quickly and simply are preferable. For example, the method of defining Pe1 and Pe2 after detecting the eye-outline using edge-detection or detecting Pe1 and Pe2 using corner-detection can preferably be used.

Using a given method, the pupil detection part 132 detects the left end Pp1 and the right end Pp2 of the pupil 252 in the face image as shown in FIG. 4. The method of detecting the both ends of the pupil 252 is not limited to a particular method. The methods capable of detecting them more accurately, quickly and simply are preferable. For example, the method of detecting the left end Pp1 and the right end Pp2 after detecting the outline of the pupil 252 using edge-detection can preferably be used.

The feature parameter calculation part 144 calculates the feature parameter showing a correlation of the both eye ends Pe1 and Pe2 with respect to the both pupil ends Pp1 and Pp2. For example, the feature parameter can be the relative coordinate of the eye end Pe1 with respect to the pupil end Pp1, in other words, the vector in between the pupil end Pp1 and the eye end Pe1, and the relative coordinate of the eye end Pe2 with respect to the pupil end Pp2, in other words, the vector in between the pupil end Pp2 and the eye end Pe2. Alternatively, the ratio of the length of the both vectors can be the feature parameter. Any feature parameters represent the position of the pupil with respect to the eye-outline, more specifically with respect to parts of the eye-outline, the left end Pe1 and the right end Pe2.

Furthermore, additional parameters can be the relative coordinate of the right end Pp2 with respect to the left end Pp1 of the pupil, or the relative coordinate of the left end Pp1 with respect to the right end Pp2 and the length in between the left end Pp1 and the right end Pp2 of the pupil.

Alternatively, using a given method such as an elliptical degree in separation filter, the eye detection part 131 detects a given number of feature points Pe11 through Pe22, e.g. 12 feature points on the outline of the eye 251 as shown in FIG. 5. The method of detecting the feature points on the outline of the eye 251 is not limited to a particular method. The methods capable of detecting them more accurately, quickly and simply are preferable.

The pupil detection part 132, using a given method, detects the center Pp11 of the pupil 252 in the face image as shown in FIG. 5. The method of detecting the center Pp11 of the pupil 252 is not limited to a particular method. The methods capable of detecting it more accurately, quickly and simply are preferable.

The feature parameter calculation part 144 calculates a feature parameter showing the correlation of the feature points Pe11 through Pe22 on the outline of the eye 251 with respect to the center Pp11 of the pupil 252. For example, the feature parameter can be the relative coordinate of the feature points Pe11 through Pe22 with respect to the center Pp11, in other words, the vectors in between the center Pp11 and the respective feature points Pe11 through Pe22. Alternatively, the directions of the 12 vectors and the ratios of the lengths of respective vectors can be the feature parameter. Any feature parameters represent the position of the pupil 252 with respect to the outline of the eye 251 and a shape of the outline of the eye 251.

The feature parameters described above are merely examples. Other feature parameters representing the position of the pupil 252 with respect to the outline of the eye 251 and the shape of the eye-outline can be used. For example, in FIG. 4, the number and the positions of the feature points on the outline of the detected pupil 252 can be changed or the center of the pupil 252 can be used to create a feature parameter instead of using the feature points on the outline of the pupil 252. Further, the width and height of the outline of the eye 251 and a parameter showing the shape of the pupil can be added to the feature parameters.

According to the above description, the learning part 121 detects the feature points of the outline of the eye 251 and the pupil 252. Alternatively, a user can detect the feature points by reviewing the face image and include the coordinate of the detected feature points or the feature parameters calculated from the detected feature points into the face data.

In the above example, description is made to the right eye. It goes without saying that the same process can be applied to create the feature parameters for the left eye.

In step S5, the learning data generation part 134 generates learning data. Specifically, the learning data generation part 134 generates data correlating the pupil direction of the object person with respect to the feature parameters calculated based on the face direction and the face image when the face image is shot. The learning data generation part 134 accumulates the generated learning data into the learning data accumulation part 135.

In step S6, the learning data generation part 134 judges whether a given amount of the learning data is accumulated. If judged not so, the process goes back to step S1, and the processes of steps S1 through S6 are repeatedly executed until it is judged that the given amount of the learning data is accumulated.

The user takes a shot of the face image of the object person with the face direction and pupil direction changing and inputs to the learning part 121 the shot face image and the data showing the face direction and the pupil direction of the object person when the face image is shot, thus the processes of steps S1 through S6 are repeatedly executed. In this way, the feature parameters are calculated based on multiple different combinations of the face directions and the pupil directions of the object person and the learning data with respect to the different respective combinations is accumulated.

It is preferable to collect the learning data based on a large number of combinations of the face directions and the pupil directions and to collect the learning data based on a large number of the object persons for accurately analyzing the correlation of the face direction and the feature parameter with respect to the pupil direction in the later described processes. Moreover, it is preferable to select the object persons diversified in age, gender, shape of face and positions of respective face parts.

In step S6, the learning data generation part 134, when judging that a given amount of the learning data is accumulated, notify it to the correlation analysis part 136 and the process goes to step S7.

In step S7, the correlation analysis part 136, using a given method, analyzes the correlation of the face direction and the feature parameter with respect to the pupil direction based on the learning data accumulated in the learning data accumulation part 135. The method of analyzing the correlation is not limited to a particular method. The methods capable of analyzing it more accurately, quickly and simply are preferable.

Figure 6:
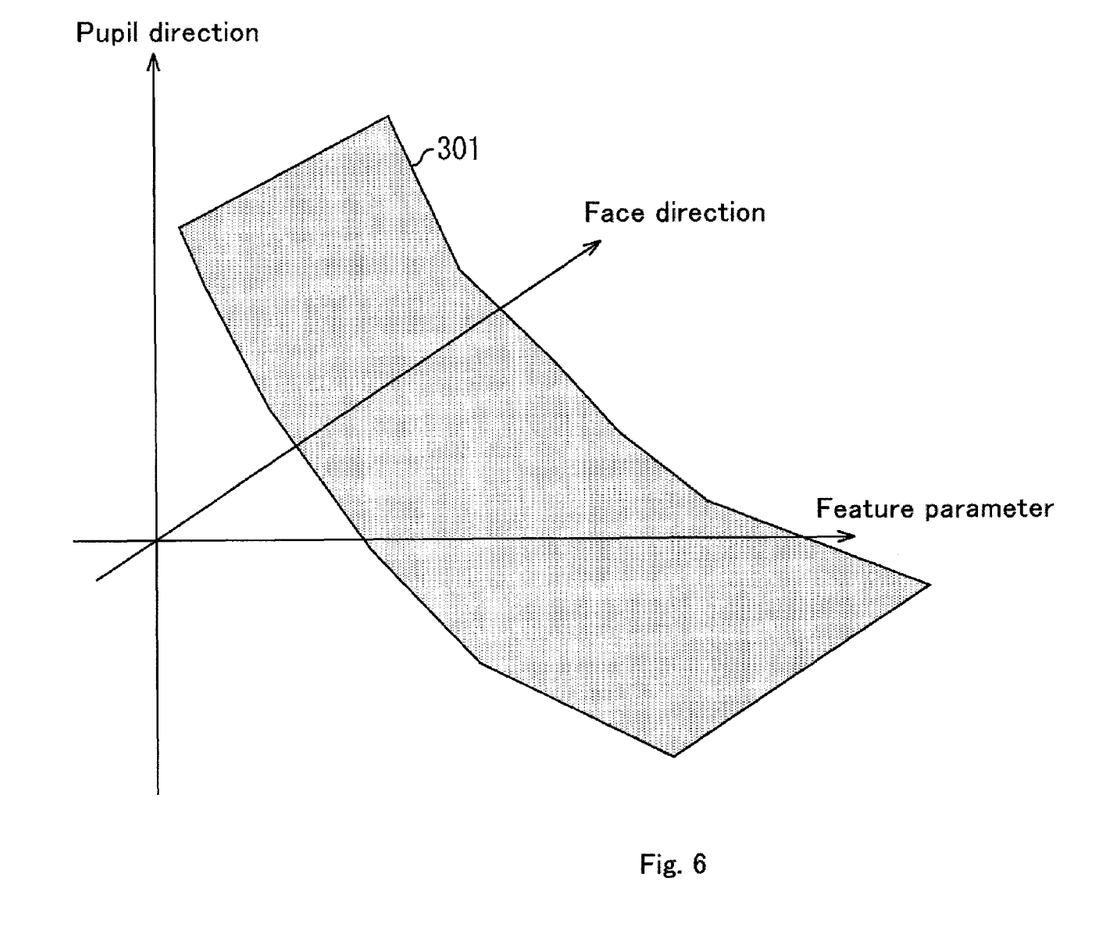
FIG. 6 is a schematic view illustrating a hyperplane representing a distribution of learning data.

For example, as shown in FIG. 6, the distribution of the learning data is approximated by a hyperplane 301 in a coordinate space with axes of the feature parameters, the face direction and the pupil direction The correlation analysis part 136 calculates the approximation representing the hyperplane 301 as the correlation of the face direction and the feature parameter with respect to the pupil direction, for example by Canonical Correlation Analysis (CCA). In the coordinate space shown in FIG. 6, the feature parameter is represented by a single axis for ease of explanation, but actually the same number of axes are provided for the respective parameters included in the feature parameter.

In step S8, the correlation analysis part 136 outputs the analysis results. The correlation analysis part 136 outputs to the pupil direction estimation part 145 the data showing the analysis results of the correlation of the face direction and the feature parameter with respect to the pupil direction. After that, the learning process terminates.

Figure 7:
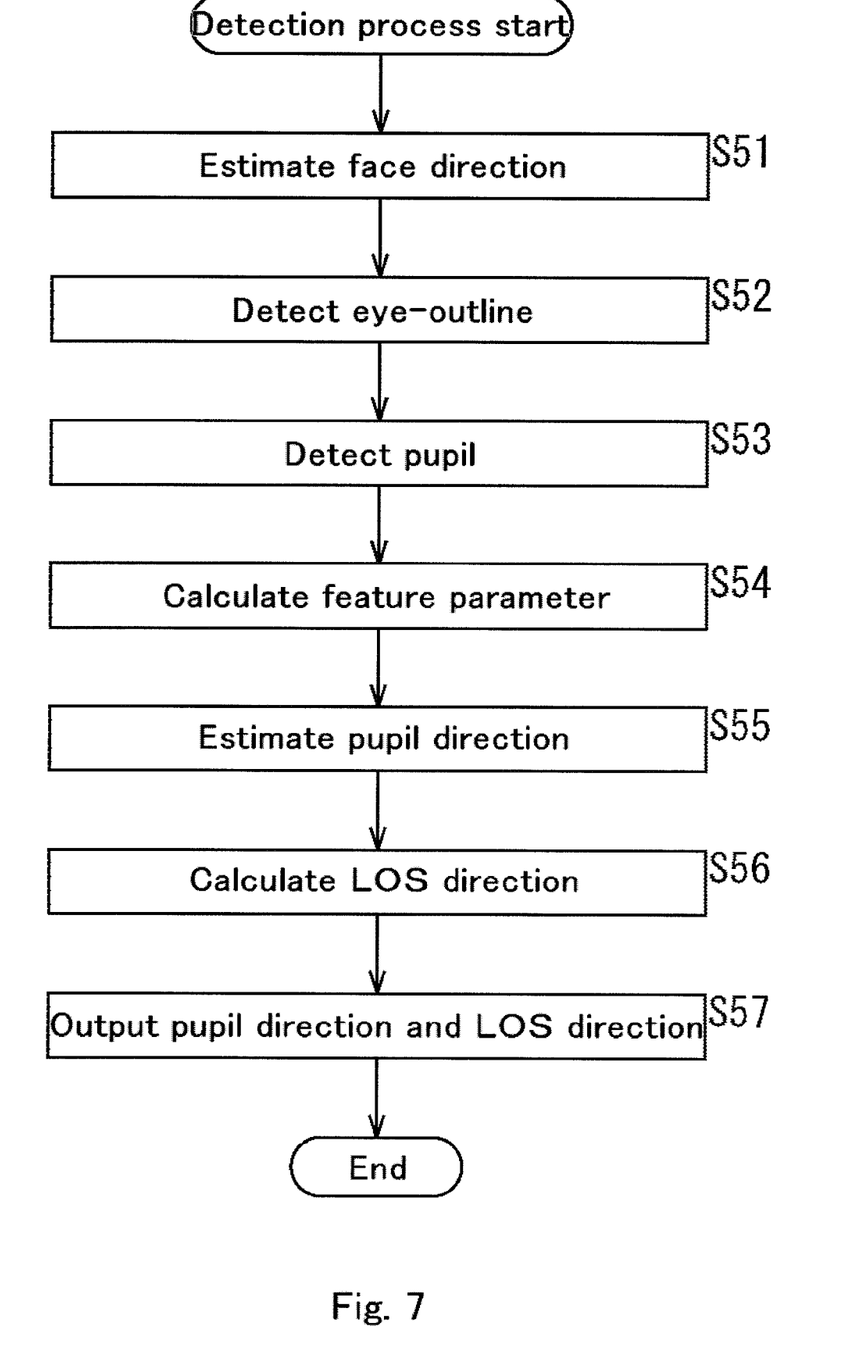
FIG. 7 is a flow chart showing detecting processes.

Next, the detection process executed by the LOS detection device 112 is described in reference to the flowchart shown in FIG. 7. The process starts when the face image of the object person shot by the camera 111 enters to the face direction estimation part 141.

In step S51, the face direction estimation part 141 estimates the face direction. Specifically, the face direction estimation part 141, using a given method, estimates the face direction of the object person appearing in the face image. The method of estimating the face direction is not limited to a particular method. The methods capable of estimating it more accurately, quickly and simply are preferable. The face direction estimation part 141 sends the face image and the data showing the estimation results to the eye detection part 142. Further, the face direction estimation part 141 sends the data showing the estimation results to the pupil direction estimation part 145 and the LOS direction calculation part 146.

Figure 3:
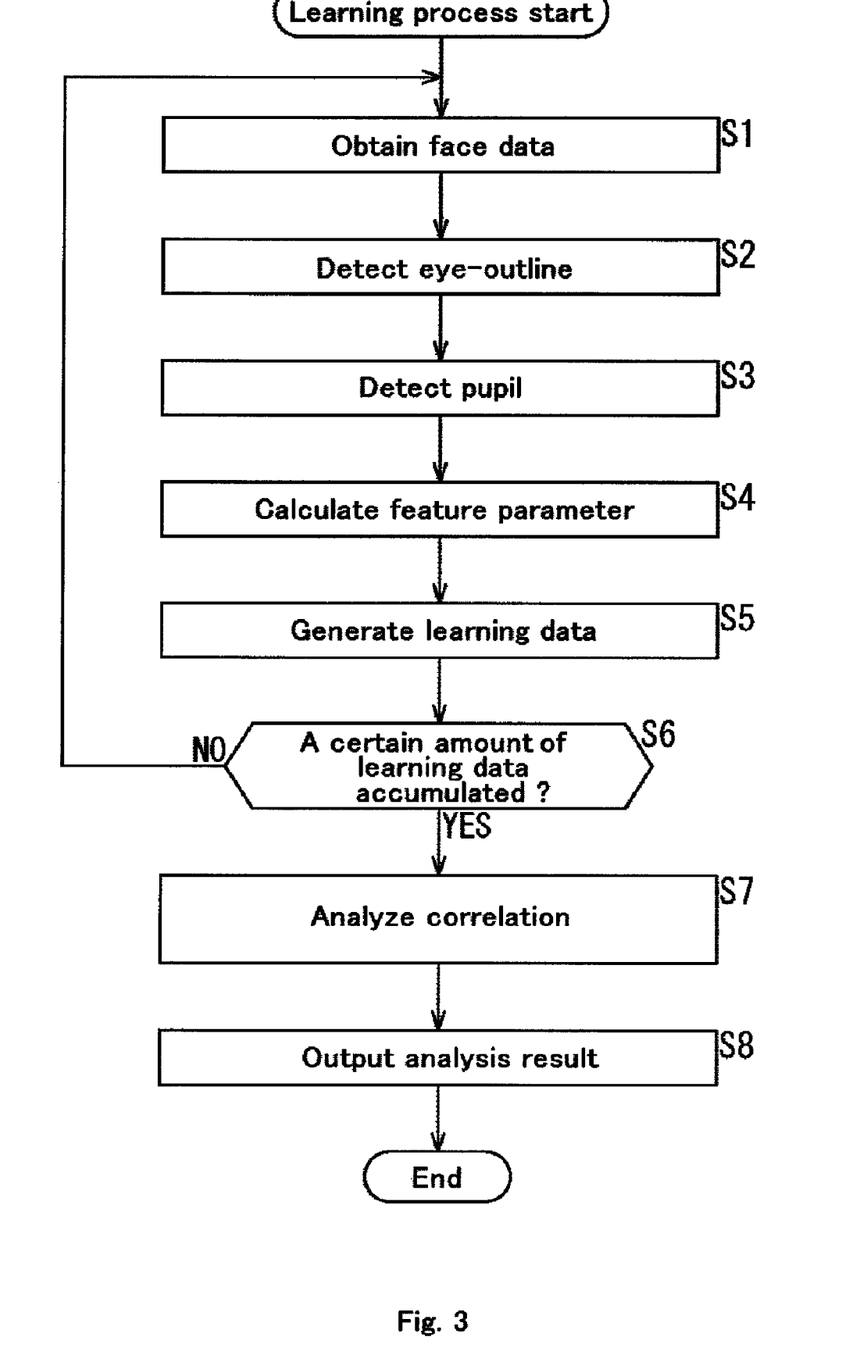
FIG. 3 is a flow chart showing a learning process.

In step S52, the eye detection part 142 detects the eye-outline in the face image of the object person in the same process as that of the eye detection part 131 in step S2 of FIG. 3. The eye detection part 142 sends the face image and the data showing the detection results to the pupil detection part 143. Further, the eye detection part 142 sends the data showing the detection results to the feature parameter calculation part 144.

In step S53, the pupil detection part 143 detects the pupil in the face image of the object person in the same process as that of the pupil detection part 132 shown in step S3 of FIG. 3. The pupil detection part 143 sends the data showing the detection results to the feature parameter calculation part 144.

In step S54, the feature parameter calculation part 144 calculates the feature parameter based on the eye-outline and detection results of the pupil of the object person in the same process as that of the feature parameter calculation part 133 shown in step S4 of FIG. 3. The feature parameter calculation part 144 sends the data showing the calculated feature parameter to the pupil direction estimation part 145.

In step S55, the pupil direction estimation part 145 estimates the pupil direction. Specifically, the pupil direction estimation part 145 estimates the pupil direction by applying the face direction estimated by the face direction estimation part 141 and the feature parameter calculated by the feature parameter calculation part 144 to the correlation of the face direction and the feature parameter with respect to the pupil direction, the correlation being analyzed by the correlation analysis part 136. As described above, the feature parameter represents the position of the pupil in the eye-outline or the position of the pupil in the eye-outline and the shape of the eye-outline. In other words, the pupil direction estimation part 145 estimates the pupil direction of the object person based on the correlation of the pupil position in the eye-outline and the face direction with respect to the LOS direction, and the pupil direction in the eye-outline and the face direction of the object person. Alternatively, the pupil direction estimation part 145 estimates the pupil direction of the object person based on the pupil position in the eye-outline and the correlation of the face direction and the shape of the eye-outline with respect to the LOS direction, and the pupil position in the eye-outline, the face direction and the shape of the eye-outline of the object person. The pupil direction estimation part 145 sends the data showing the estimated pupil direction to the LOS direction calculation part 146.

In step S56, the LOS direction calculation part 146 calculates the LOS direction. Specifically, the LOS direction calculation part 146 calculates the LOS direction of the object person by adding the face direction estimated by the face direction estimation part 141 to the pupil direction estimated by the pupil direction estimation part 145. For example, if the face direction is estimated horizontally $\Theta_{fx°}$, vertically $\Theta_{fy°}$ and the pupil direction is estimated horizontally $\Theta_{px°}$, vertically $\Theta_{py°}$, then LOS horizontal and vertical directions $\Theta_{sx°}$ and $\Theta_{sy°}$ are calculated by the following formulas (1) and (2) respectively.

$$\Theta_{sx°}=\Theta_{fx°}+\Theta_{px°} \quad (1)$$

$$\Theta_{sy°}=\Theta_{fy°}+\Theta_{py°} \quad (2)$$

In step S57, the detection part 122 detects the pupil direction and the LOS direction. Specifically, the pupil direction estimation part 145 outputs the data showing the estimated pupil direction to the latter stage of the LOS detection device 112 and the LOS direction calculation part 146 outputs the data showing the calculated LOS direction to the latter stage of the LOS detection device 112. After that, the detection process terminates.

Figure 8:
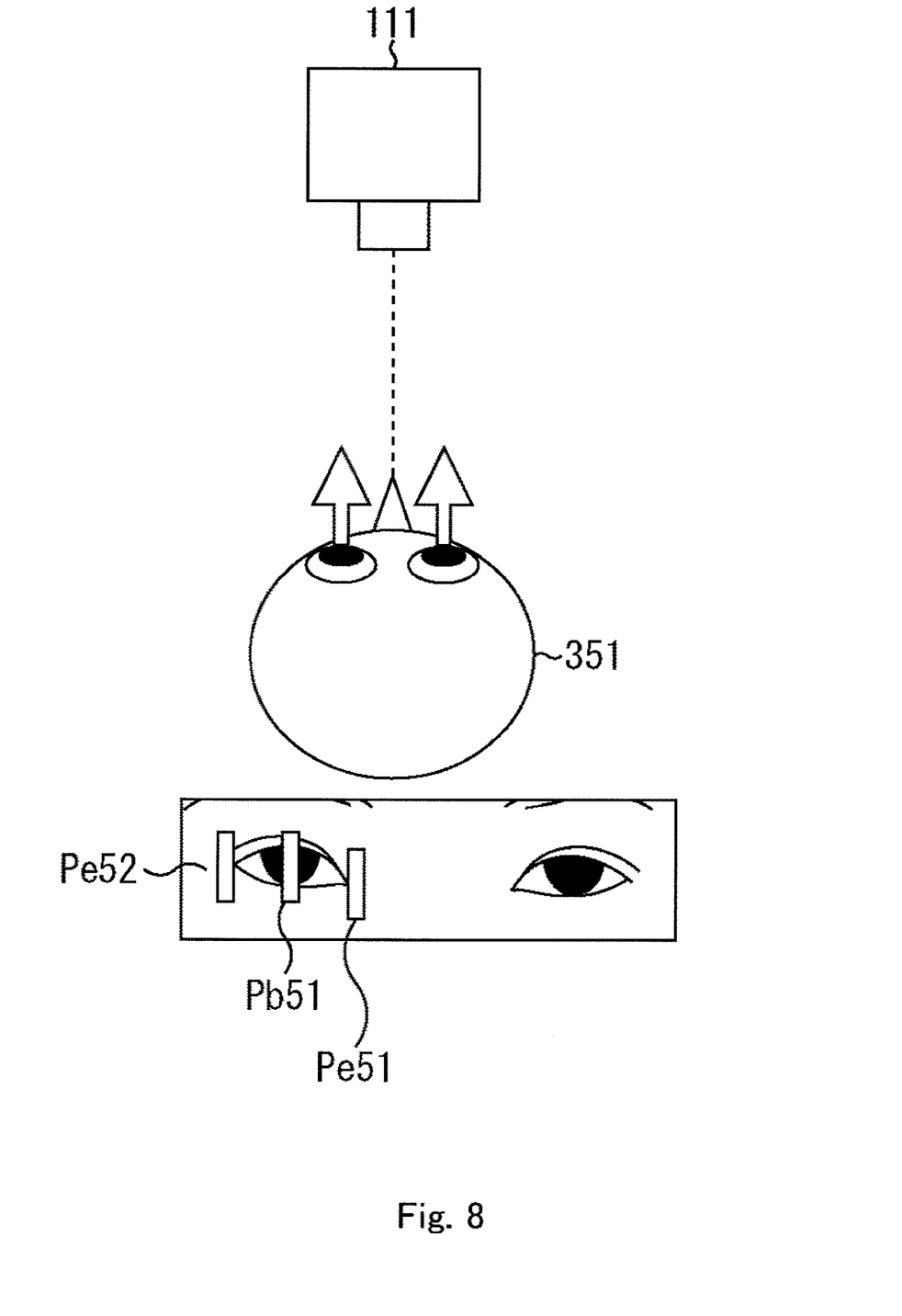
FIG. 8 is a schematic view illustrating the effect of an embodiment of the present invention.
Figure 9:
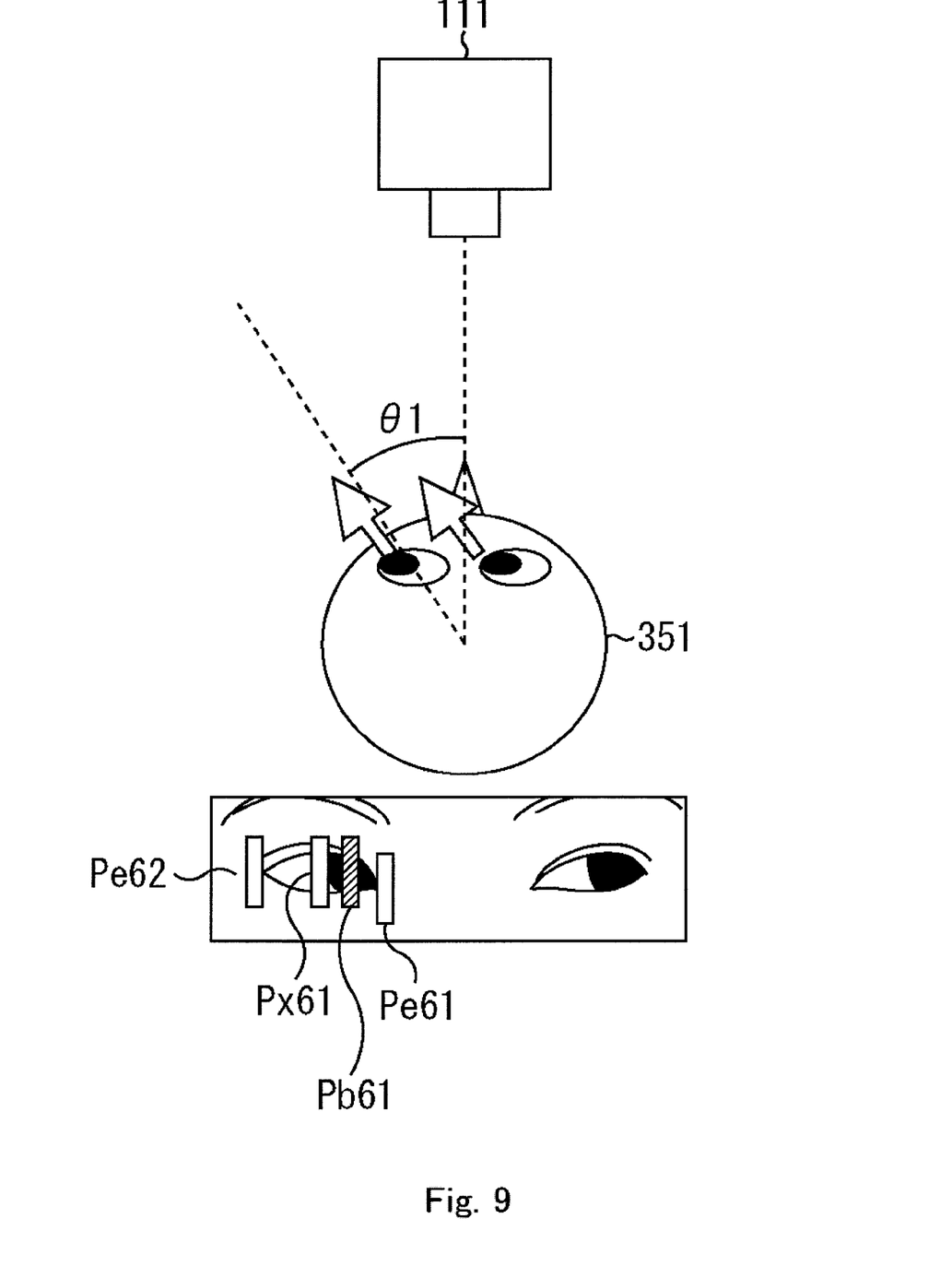
FIG. 9 is a schematic view illustrating the effect of an embodiment of the present invention.
Figure 10:
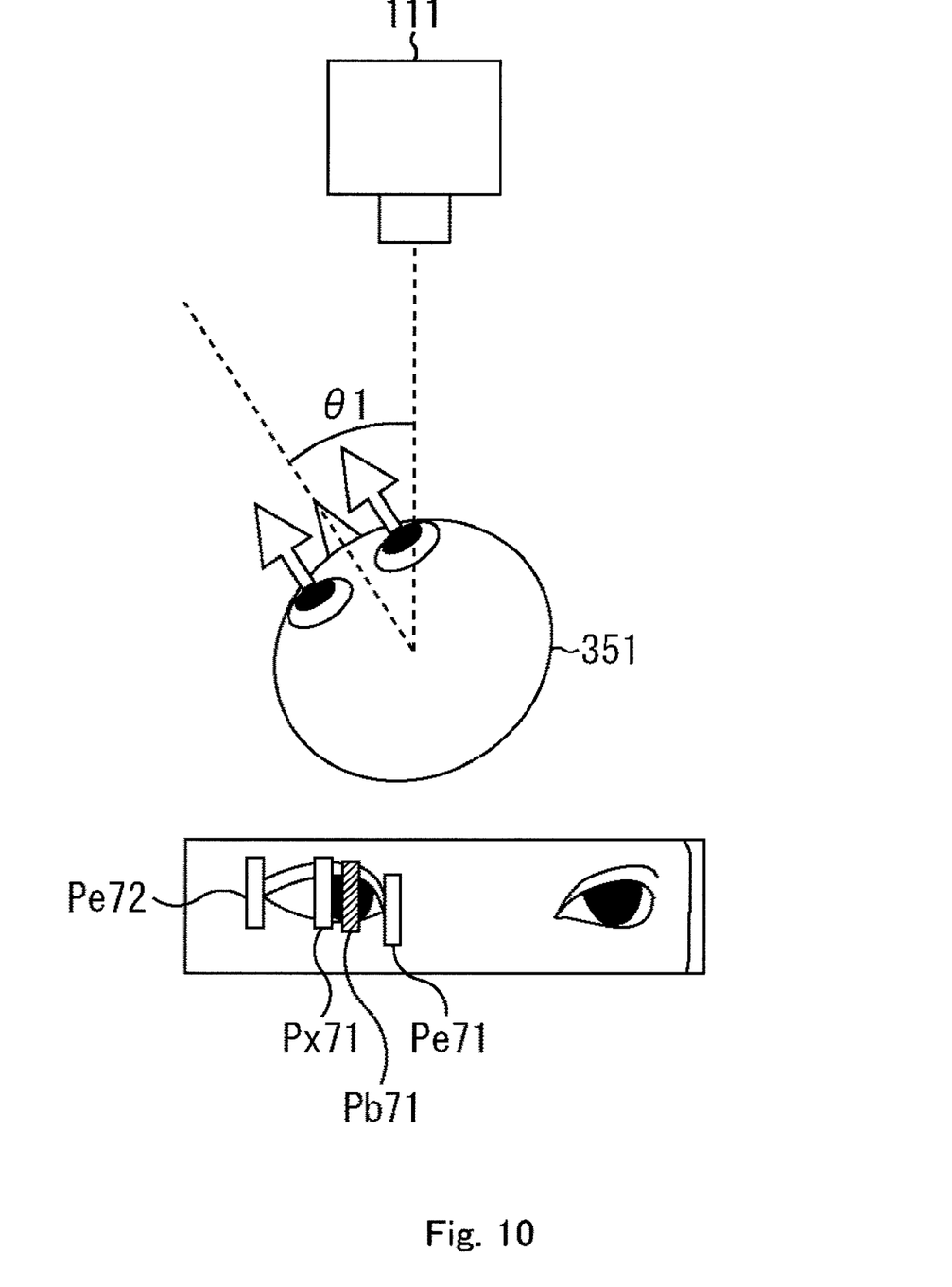
FIG. 10 is a schematic view illustrating the effect of an embodiment of the present invention.

In this way, the pupil direction and the LOS direction of the object person can be accurately detected regardless of face directions of object persons or differences among individuals. FIGS. 8 through 10 illustrate examples of detecting pupil directions with different face directions in reference to the center position of the pupil with respect to the both eye ends when the face and the LOS of the object person are directed to front face.

FIG. 8 shows an example of positions of left-end eye Pe51, right-end eye Pe52 and pupil center Pb51 when the face and the pupil of an object person 351 are facing toward the camera 111. The pupil direction is detected as described below based on the positional relation of the pupil center Pb51 to the left-end eye Pe51 and the right-end eye Pe52.

As shown in FIG. 9, when the pupil is directed leftwards at $\Theta_1°$ with the face of the object person 351 facing toward the camera 111, the right-end eye Pe61 and the left-end eye Pe62 are detected at substantially the same positions as those of the right-end eye Pe51 and the left-end Pe52 shown in FIG. 8. In this case, the reference position Px61 for determining the pupil direction of the object person 351 is set so that the length in between the right-end eye Pe61 and the reference position Px61: the length in between the reference position Px61 and the left-end eye Pe62≈the length in between the right-end eye Pe51 and the pupil center Pb51: the length in between the pupil center Pb51 and the left-end eye Pe52, thus the reference position Px61 is set nearly at the same position as that of the pupil center Pb51 shown in FIG. 8. Accordingly, the pupil direction of the object person 351 can be accurately detected as it is directed leftwards at $\Theta_1°$ based on the actual difference between the pupil center Pb61 and the reference position Px61.

On the other hand, as shown in FIG. 10, when the pupil is directed in front face with the face of the object person 351 facing leftwards at $\Theta_1°$ to the camera 111, the reference position Px71 is set so that that the length in between the right-end eye Pe71 and the reference position Px71: the length in between the reference position Px71 and the left-end eye Pe72≈the length in between the right-end eye Pe51 and the pupil center Pb51: the length in between the pupil center Pb51 and the left-end eye Pe52. The pupil direction is falsely detected as it is directed leftwards despite it is directed in front face (0°) because the actual pupil center Pb71 is displaced leftwards from the reference position Px71.

The LOS direction detection device 112 can accurately estimate the pupil direction of the object person 351 even if the object person 351 does not face toward the camera 111 as shown in FIG. 10, because, as described above, the pupil directions are estimated based on the data showing the pupil positions with respect to the eye-outline in the multiple combinations of the face directions and the pupil directions.

It becomes possible to accurately detect the pupil direction and the LOS direction by learning the above described correlation, thus flexibly responding to various conditions and environments where the LOS detection system 101 is used, for example, the performances of the camera 111 or the positions where it is installed.

In the above description, the pupil direction is used for the face data and the learning data. Instead of the pupil direction, the LOS direction, i.e. the direction of the LOS viewed from the camera 111 can be used. Thus, following that the LOS direction of the object person is estimated in step S55 of FIG. 7 as described above, the pupil direction can be calculated in step S56 based on the face direction and the LOS direction of the object person.

If the object persons are specific individuals, the more accurate detection of the pupil direction and the LOS direction becomes possible by measuring the learning data for the each individual and analyzing and utilizing the correlation for the each individual.

One or more embodiments of the present invention can be applied to devices using the LOS and the view points of users, for example, a camera for controlling shooting by detecting the LOS of an object person, a driving support device for supporting a driver detecting the driver's LOS, a display for controlling displaying based on a user's view point and a suspicious individual detecting device for detecting suspicious individuals by detecting changes in suspicious persons' LOS.

The processes described above can be executed by a hardware or by a software. If it is executed by a software, the program configuring the software can be built in a device or installed through a program recording media in a general-purpose personal computer for executing a various functions with a various programs installed.

Figure 11:
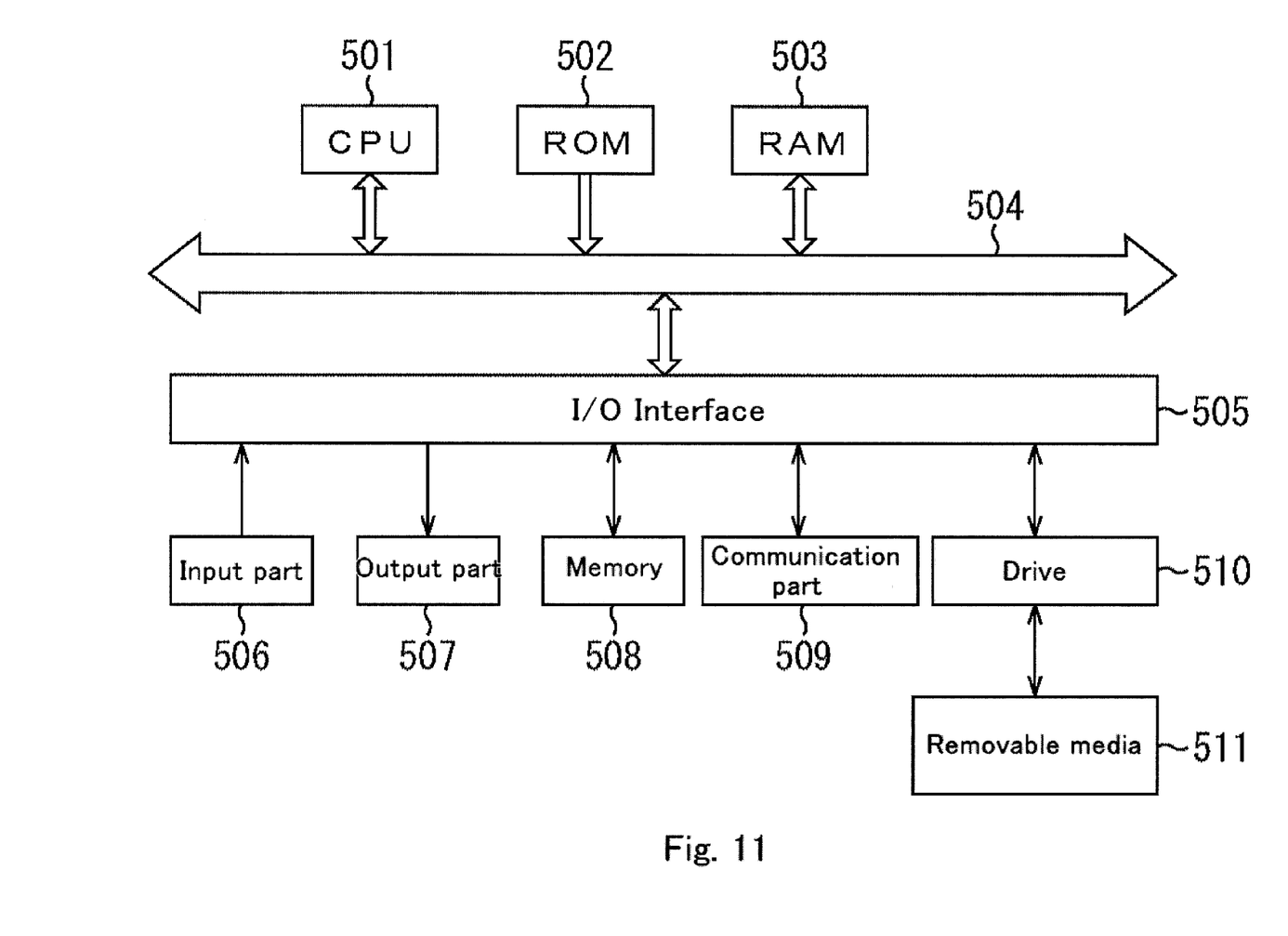
FIG. 11 is a block diagram showing an example of a computer configuration.

FIG. 11 is a block diagram showing an example of a configuration of a computer for executing programs of above described processes. CPU (Central Processing Unit) 501, ROM (Read Only Memory) 502 and RAM (Random Access Memory) 503 are mutually connected by bus 504.

The bus 504 is connected to IO interface 505. The IO interface 505 is connected to input part 506 including a keyboard, mouse and microphone, output part 507 including a display and a speaker, memory 508 including a hard disc and nonvolatile memory, communication part 509 including a network interface and a drive 510 for driving removable media 511 including a magnetic disc, a photo disc, a photomagnetic disc or a semiconductor memory.

In a computer configured above, the CPU 501 loads the programs stored in the memory 508 into the RAM 503 through the IO interface 505 and the bus 504 and executes them, thus the above described processes are executed.

The programs executed by the computer are provided by a packaged removable media such as a magnetic disc including a flexible disc, CD-ROM, DVD, a photomagnetic disc or a semiconductor memory or provided through a wired or wireless transmission media such as LAN, internet and digital satellite broadcasting.

The programs can be installed in the memory 508 through IO interface 505 by loading the removable media 511 to the drive 510. Alternatively, the programs can be received by the communication part 509 through a wired or wireless transmission media and installed in the memory 508. Furthermore, the programs can be previously installed in the ROM 502 or memory 508.

The programs executed in the computer can be executed in time series according to the order described in the present specification, or can be executed in parallel or upon a calling when it is requested.

The term "system" used in the present specification means an overall device configured with multiple devices and means.

In the above description and drawings are only to be illustrative of exemplary embodiments which achieve the aspects and advantages described above. Modifications of, and substitutions to, specific operating conditions and structures can be made without departing from the spirit and scope of the invention.

Accordingly, the claimed invention is not to be considered as being limited by the foregoing description and drawings, but is only limited by the scope of the appended claims.

What is claimed is:

1. A line of sight detecting device, comprising:
    face direction estimation means for estimating a face direction of an object person based on a shot face image of the object person;
    eye detection means for detecting a part of an eye outline in the face image of the object person;
    pupil detection means for detecting a pupil in the face image of the object person; and
    line of sight direction estimation means for estimating a direction of a line of sight of the object person based on a correlation of a pupil position in the eye outline and the face direction with respect to the direction of the line of sight,
        wherein the line of sight direction estimation means estimates the line of sight direction of the object person based on the correlation of the pupil position, the face direction and a shape of the eye outline with respect to the line of sight direction, and the pupil position, the face direction and the shape of the eye outline of the object person.

2. The line of sight detecting device according to claim 1, further comprising:
    correlation analysis means for analyzing the correlation based on data of the pupil positions in multiple combinations of the face directions and the line of sight directions,
    wherein the line of sight direction estimation means estimates the direction of the line of sight of the object person based on the correlation analyzed by the correlation analysis means.

3. A line of sight detecting method performed by a detection device, the method comprising:
    estimating a face direction of an object person based on a shot face image of the object person;
    detecting a part of an eye outline in the face image of the object person;
    detecting a pupil in the face image of the object person; and
    estimating a direction of a line of sight of the object person based on a correlation of a pupil position in the eye outline and the face direction with respect to the direction of the line of sight,
    wherein with respect to the step of estimating the direction of the line of sight of the object person, the line of sight direction of the object person is based on the correlation of the pupil position, the face direction and a shape of the eye outline with respect to the line of sight direction, and the pupil position, the face direction and the shape of the eye outline of the object person.

4. A program storage device readable by a computer tangibly embodying a program of instructions executable by the computer to perform a method comprising:
    estimating a face direction of an object person based on a shot face image of the object person;
    detecting a part of an eye outline in the face image of the object person;
    detecting a pupil in the face image of the object person; and
    estimating a direction of a line of sight of the object person based on a correlation of a pupil position in the eye outline and the face direction with respect to the direction of the line of sight,
    wherein with respect to the step of estimating the direction of the line of sight of the object person, the line of sight direction of the object person is based on the correlation of the pupil position, the face direction and a shape of the eye outline with respect to the line of sight direction, and the pupil position, the face direction and the shape of the eye outline of the object person.

* * * * *